United States Patent [19]

Silvetti, Sr. et al.

[11] Patent Number: 5,177,065
[45] Date of Patent: Jan. 5, 1993

[54] MONOSACCHARIDE CONTAINING WOUND HEALING PREPARATION

[76] Inventors: Anthony N. Silvetti, Sr.; Anthony N. Silvetti, Jr., both of 930 Ashland Ave., River Forest, Ill. 60305

[21] Appl. No.: 633,878

[22] Filed: Dec. 26, 1990

[51] Int. Cl.⁵ .................. A61K 31/715; A61K 31/79; A61K 7/06; A61K 37/12
[52] U.S. Cl. ........................ 514/53; 514/54; 424/70; 530/357
[58] Field of Search .............. 514/53, 54; 424/80, 424/70, 71; 530/357

[56] References Cited

U.S. PATENT DOCUMENTS

| | | | |
|---|---|---|---|
| 3,950,282 | 4/1976 | Gilbert et al. | 536/32 |
| 4,241,090 | 12/1980 | Stroz et al. | 426/658 |
| 4,264,573 | 4/1981 | Powell et al. | 424/80 |
| 4,311,722 | 1/1982 | Vink et al. | 426/658 |
| 4,726,943 | 2/1988 | Klueppel et al. | 424/49 |
| 4,889,844 | 12/1989 | Silvetti et al. | 514/23 |
| 4,971,806 | 11/1990 | Cherukuri et al. | 426/5 |

*Primary Examiner*—Johnnie R. Brown
*Assistant Examiner*—Everett White
*Attorney, Agent, or Firm*—Scully, Scott, Murphy & Presser

[57] ABSTRACT

A composition comprising either fructose or ribose, starch hydrolysate and a film forming agent other than starch hydrolysate is described. The composition, characterized by a weight ratio of fructose or ribose to starch hydrolysate in the range of between about 1:99 and about 15:85, is employed in a method of treating wounds in a host in need of such treatment. In this method a therapeutically effective amount of the composition contacts the wound for a period of time sufficient to initiate wound healing.

14 Claims, No Drawings

MONOSACCHARIDE CONTAINING WOUND HEALING PREPARATION

FIELD OF THE INVENTION

The present invention relates to methods and compositions for beneficiating wound healing. More specifically, it relates to the use of monosaccharides, especially fructose, to beneficiate wound healing processes

BACKGROUND OF THE INVENTION

During the period following development or infliction of serious physical damage to the skin, by way of for example, severe burns, wounds, pressure ulcers, and the like, the injured area is extremely unstable physiologically; following such injury or trauma, the normal physiological processes of the area in question may be severely compromised. Disruption in the normal pattern of skin growth, blood flow, and immunity may all be impaired to some extent by the trauma to the region The physician treating such damaged tissue must therefore be able to control and eventually reverse these undesirable effects, while at the same time stimulating the processes that are necessary to achieve healing of the area.

Because of the variety of different systems which may be adversely affected by such injury, it is difficult to find a single agent which will be effective in controlling the various sources of the problems For example, one of the most severe difficulties encountered is the immediate colonization of the wound by a variety of different types of microbial species. Common invaders of a wound site are such known pathogens as *Staphylococcus aureus*, as well as a number of opportunistic pathogens, such as *Escherichia coli* or *Pseudomonas aeruginosa*. Various yeasts, particularly *Candida albicans*, may also be found at the wound. Although a number of antimicrobial agents for topical application are known, none has proven to be without some serious disadvantage. For example, silver sulfadiazine, the current antibacterial agent of choice is effective against gram-positive bacteria and gram-negative but many resistant strains have developed in the course of its use, particularly in the genus Pseudomonas. Similarly, the commonly used Betadine (povidone-iodine), although effective against both gram-positive and gram-negative bacteria, can be quite painful to the patient upon application, kills white cells in the wound, specifically polymorphonuclear cells, lymphocytes, monocytes, and macrophages, and may cause sensitization of an area already severely traumatized. Other known antibacterial agents may be hampered in their use by low diffusibility of the composition, or a range of activity that covers relatively few types of microbes; expense, as with substances such as the various silver salts, is also a factor to be considered.

Related to the invasion by microbes of the wound site is the generally decreased circulation which is also observed in many cases. For example, in decubitus or stasis ulcers, a cessation of blood flow may develop gradually, whereas an acute cessation of flow may occur in thermo-radiation and chemical burns. In either case the decrease in the rate of blood flow means a corresponding decrease in the provision to the cells of nutrients and oxygen. Thus deprivation in turn leads to necrosis of tissue in the poorly supplied region, which will be followed by the invasion of the unwanted bacteria and fungi. In order for healing to proceed, the damaged area must not only be rid of any lingering microbial infection, but also must have a restored blood flow, which will provide sufficient nutrient and oxygen supply to support a regeneration of the wounded region. In the ideal situation, the increased blood flow should also be accompanied by the formation of healthy granulation tissue. The latter is a layer of highly vascularized tissue, containing numerous fibroblasts and collagen and ground substance, which supports the normal wound healing processes of recollagenation and reepithelialization.

Another very critical aspect of the wound healing process is the initiation of wound closure. This is generally a two-stage process, comprising contraction and epidermal migration. Contraction is the process of bulk skin movement from the edges of the wound, while migration is the separation and movement of activated epidermal cells over the surface of the wound. Because contraction itself may lead to some scarring it is preferable to be able to speed healing in a manner which will increase the process of epidermal migration. The process of migration is characterized by a stimulation of mitosis in the epidermal cells, accompanied by movement across the wound site. The extent to which epidermal migration, and thus wound closure, can be promoted will also in some cases determine whether or not additional skin grafting is required to complete the healing of the wound.

It is thus evident that a large number of different factors must be controlled and/or stimulated in order to achieve thorough regeneration of the damaged tissue. Since the processes involved, and the mechanisms controlling them, are so diverse, it has proven difficult to pinpoint a single treatment composition or method which is capable of aiding and promoting most or all of the required processes simultaneously. As noted above with respect to the various antibacterial agents available, the majority of wound healing compositions available suffer from one or another deficiencies, whether it be in complexity of application, insufficient ability to control infection, irritation caused to the patient, limited range of protective activity, or expense (See for example D. Wise (ed.) *Burn Wound Coverings*, Vol. I Chap. I, p. 11-22, CRC Press, 1984)

It has now been surprisingly discovered that certain monosaccharides, when used either alone or in combination with many known wound treating compositions, may have the effect of providing added protection against microbial infection, enhancing the growth of granulation tissue, promoting the vascularization of the wound site, and/or stimulating the process of epidermal migration and wound closure. When the monosaccharides are used in combination with known compositions, the effects observed on wound healing are significantly and unexpectedly improved with respect to the above features. When used alone, the monosaccharides show a remarkable and unpredicted effect on control of bacterial infection on damaged skin. The monosaccharide fructose has proven to be most useful and successful in this regard.

Various monosaccharides have previously been known to be used for therapeutic purposes. For example, it is known to administer fructose intravenously to inhibit erythrocyte fragility during surgical extracorporeal circulation procedures (U.S. Pat. No. 4,448,771). Sorbose is also known (U.S. Pat. No. 4,390,523) to be used as a sugar substitute to inhibit acid formation by bacteria in the mouth, but it does not itself have an effect on bacterial growth. Oral administration of pure fructose is also known to control human stress response (U.S. Pat. No. 4,024,250). Bacteriostatic effects have also been attributed to irradiated glucose and fructose, but this effect is the apparent result of the peroxide compounds produced by the irradiation (Namike et al. *Agr. Biol.Chem.* 37(5): 989-998, 1973). The latter reference, in fact, shows normal bacterial growth in the presence of glucose and fructose. Various natural substances, such as honey or sugar (i.e., sucrose) have also been traditionally used as a type of folk-medicine for preventing infection. Thus, there has been no previous indication that monosaccharides would have any antibacterial effect either alone or in combination with other products for a topical wound healing preparation, and in fact, the monosaccharides show a more marked protective effect than disaccharides such as sucrose and lactose. As employed herein, the term wound is intended to apply to any skin or connective tissue trauma, such as thermal burns, pressure ulcers, ischemic ulcers, chemical and radiation burns, abcesses, fistulae, bone defects, malunion of fractures, vasculitis, tropical parasitic ulcers, leprosy ulcers, and acne or psoriasis lesions.

BRIEF DESCRIPTION OF THE INVENTION

The present invention relates to a composition comprising an effective amount of at least one pharmaceutically acceptable monosaccharide containing from about 3 to 7 carbon atoms and a pharmaceutically acceptable film forming agent. In its preferred embodiment, the present invention relates to a composition comprising an effective amount of fructose and a starch hydrolysate, and preferably to a composition comprising fructose and a starch hydrolysate having a dextrose equivalent of between 13 and 17. These compositions are useful both in the treatment and healing of wounds, as well as for use as carriers for other dermatological treatment agents to be used in salve form.

The present invention also provides a method of treating wounds which comprises contacting the wound with the compositions described above for a period of time sufficient to initiate wound healing.

DETAILED DESCRIPTION OF THE INVENTION

In addition to being useful alone as an antibacterial pretreatment for wounds, as described in co-filed and copending application Ser. No. 06/790,044, filed Oct. 22, 1985, now abandoned, the monosaccharides also provide an unexpectedly beneficial effect when used as an addition to traditional wound healing compositions. Particularly good effects have been observed when a monosaccharide is added in a therapeutically effective amount to various film forming agents which are routinely used as protective coverings for various types of wounds, especially burns. These agents in themselves form a simultaneous barrier to both water and microbes, and as used herein, comprise various types of dry (non-gel) films, as well as biological gels (gelatin and gelatin/pectin materials), synthetic hydrogels, ionic gels and adhesives. Although monosaccharides may be effectively combined and used with any of the above materials, unusually favorable results are achieved by combining a monosaccharide, especially fructose, with a film-forming starch hydrolysate.

The therapeutic use of starch hydrolysate has been described in depth in U.S. Pat. Nos. 3,812,252 and 4,414,202, the teachings of which are incorporated herein by reference. In brief, this material itself has been shown to be an exceptionally effective treatment for burns, ulcers, lesions, etc. The starch hydrolysate forms a film which ultimately adheres to underlying tissue and which is semipermeable to gas and fluid. It thus provides a covering which reduces plasma and fluid loss, while also preventing invasion by pathogenic microbes. The effects observed with use of starch hydrolysate are far superior to results seen with use of traditional wound coverings. When used in combination with a monosaccharide the effects on wound healing are tremendously enhanced, producing results which heretofore have not even been possible with the use of starch hydrolysate alone.

For example, application of a mixture of a starch hydrolysate with a monosaccharide, particularly glucose or fructose, has a remarkable effect on the process of revascularization of the wound. Within 15 minutes-6 hours of such application, the treatment wound takes an intensely bright red color, visual evidence of the fact that new blood vessels are being formed in the region, and that normal circulation is returning to the site. Although it is part of the normal healing process that revascularization will eventually occur, the speed with which new blood vessels return to the damaged tissue when treated with starch hydrolysate and fructose is unexpectedly faster than that observed with starch hydrolysate alone. The presence of the added monosaccharide thus has a synergistic effect when combined with the starch hydrolysate, the end results being unattainable with either of the two substances used alone.

Similar surprising effects are seen in the development of granulation tissue. As noted above, the noticeable appearance of healthy granulation tissue signifies the start of the process of healing, to a large extent by virtue of a reconstruction of the connective tissue in the injured region by the numerous fibroblasts associated with granulation tissue. The use of starch hydrolysate alone does, to some degree, have a beneficial effect on promoting formation of granulation tissue; such tissue, where starch hydrolysate alone is used, has a relatively smooth appearance. On the other hand, when starch hydrolysate is used in combination with a monosaccharide, the granulation tissue takes on a significantly different appearance, being very intensely granular, with a rough surface, indicating a greater level of activity in the tissue thus leading to a more rapid rate of healing.

Particularly remarkable, however, is the effect the added monosaccharide has on the process of wound closure. This process is extremely important in the progression of healing, since if it proceeds to completion, the necessity for skin grafts will be minimized or avoided completely. One of the major problems with many of the known film forming agents is that they rarely are capable of enhancing the wound closing process, so that, in a wound of any substantial size, a skin graft will always be required. Starch hydrolysate alone has been shown to have a dramatic effect on the process, and does significantly reduce the necessity for skin grafting. However, when combined with a monosaccharide, the results observed with respect to wound closure are truly outstanding, with much larger wounds showing complete closure in a relatively shorter period of time than has previously been known to be possible. The effect of the added monosaccharide shows itself particularly in the stimulation of epidermal mitosis and migration; this can be demonstrated both macroscopically and microscopically. Thus, the use of a composition containing both starch hydrolysate and a monosaccharide, preferably fructose, can effectively reduce or eliminate the need for a skin graft to a far greater extent than is possible with any known wound coverings.

Finally, of course, the added monosaccharide has an antibacterial effect in conjunction with the starch hydrolysate. Whereas the starch hydrolysate alone is known to have a significant ability to control the level of bacterial infection in a wound, when combined with a monosaccharide, this ability is so enhanced as to virtually completely inhibit microbial growth at the site of application. Thus, with all the superior effects observed with the application of the film-forming agent -monosaccharide combination, the present compositions provide an exceptional method of treatment for damaged or injured tissue.

The composition of the present invention is comprises an effective amount of at least one pharmaceutically acceptable monosaccharide containing from about 3 to 7 carbon atoms and a pharmaceutically acceptable film-forming agent.

In a preferred embodiment, the pharmaceutically acceptable monosaccharide of the present invention is a pharmaceutically acceptable aldose sugar or a pharmaceutically acceptable ketose sugar. Among the pharmaceutically acceptable aldose sugars within the contemplation of the present invention are erythrose, threose, ribose, arabinose, xylose, lyxose, allose, altrose glucose, mannose, gulose, idose, galactose and talose Among the pharmaceutically acceptable ketose sugars preferred for use in the composition of the present invention are erythrulose, ribulose, xylulose, psicose, fructose, sorbose, tagatose, and sedoheptulose. Although either (D) or (L) isomers may be employed, the (D) form is generally preferable. Although all of the above aldose and ketose sugars may be employed as the monosaccharide component of the composition of the present invention, glucose of the aldose sugars and fructose and sorbose among the ketose sugars are particularly preferred. Overall, the ketose sugars are most particularly preferred, and of these, fructose is the most preferred monosaccharide for use in the composition of the present invention, since the proportions necessary to achieve the desired effect are smaller when fructose is used. The monosaccharide is preferably present, in an amount of between about 0.01 to about 50% by weight of the composition. Most preferably, the monosaccharide is present in an amount of between about 5 to about 30% of the weight of the composition. The monosaccharide component may also be a mixture of two or more monosaccharides. For example, high fructose corn syrups are available in powder form; these generally contain about a 95% combination of glucose and fructose, in approximately equal amounts. Such powders may be also combined with the starch hydrolysate, preferably in an amount of up to about 30%, in lieu of addition of a single monosacchride.

In another preferred embodiment of this invention tho pharmaceutically acceptable film-forming agents include, but are not limited to, any of starch hydrolysate, polyvinyl pyrollidone, polyvinyl alcohol, ethylene glycol, albumin, cellulose, gelatin, solubilized keratin, hydrocolloids such as alginate, karaya gum, gum arabic, gum tragacanth, agar, 0 and locust bean gum. Of these film-forming agents, starch hydrolysate is most preferred.

In yet another preferred embodiment of the present invention the composition comprises starch hydrolysate and a second film forming agent which is any one of the above-mentioned film forming agents. Thus, the composition of the present invention may include starch hydrolysate and polyvinyl pyrrolidone, solubilized keratin, alginate, in the form of alginic acid, sodium alginate, potassium alginate or calcium alginate, gum tragacanth, gelatin, agar, pectin, cellulose, especially methyl cellulose, guar gum or locust beam gum.

Of these combinations the use of starch hydrolysate with solubilized keratin, alginate, in the form of the acid, sodium, potassium or calcium salt, and gum tragacanth are particularly preferred.

Thus, in one preferred embodiment a composition which includes fructose, starch hydrolysate and solubilized keratin is utilized. In this composition, the components are present in an amount such that the fructose and the starch hydrolysate are present in a total concentration in the range of between about 1% and about 99% and said solubilized keratin is present in a concentration of between about 1% and about 99%, said percentages being by weight, based on the total weight of said fructose, starch hydrolysate and soluble keratin. Preferred ranges within this broad range include a combined fructose and starch hydrolysate concentration of between about 50% and about 75% wherein the solubilized keratin is representative of between about 25% and about 50%, said concentrations being by weight, based on the total weight of said components.

It should be appreciated that in the above compositions, as well as those to be discussed below, the weight ratio of fructose to starch hydrolysate is in the range of about 1:99 to about 15:85, preferably about 3:97.

Turning to the preferred embodiment wherein the composition includes fructose, starch hydrolysate and an alginate (either alginic acid or the aforementioned alginate salts), that composition comprises between about 1% to about 99% by weight combined fructose and starch hydrolysate and between about 1% and about 99% by weight alginate, said percentages based on the total weight of said components. A composition which includes between about 50% by weight combined fructose and starch hydrolysate and about 50% by weight alginate is preferred. Again, the weight ratio of fructose to starch hydrolysate is in the range of between about 1:99 and a bout 15:85, preferably about 3:97.

Another preferred embodiment comprises the composition which includes fructose, starch hydrolysate and gum tragacanth. As in the case of the use of the soluble keratin and alginate film forming agents, the range of utility is a composition in the range of about 1% to about 99% combined fructose and starch hydrolysate and between about 1% to about 99% gum tragacanth. Preferred ranges include compositions which include between about 50% to about 75% combined fructose and starch hydrolysate, wherein the weight ratio of fructose to starch hydrolysate is in the range of between about 1:99 to about 15:85 preferably about 3:97, and about 50% gum tragacanth, wherein all percentages are by weight based on the total weight of said components.

The above compositions, of course, can include any one or more of the other components mentioned herein in this disclosure.

In another preferred embodiment the sugar employed in the preferred composition of this invention is ribose, specifically beta D-ribose or beta D-2-deoxyribose, instead of fructose. Thus, in a preferred embodiment the composition comprises ribose (either beta D-ribose or beta D-2-deoxyribose) and starch hydrolysate. In a particular preferred embodiment the composition includes not only starch hydrolysate but, in addition, a second film forming agent which are the same agents recited immediately above in the discussion of the preferred compositions which include fructose and starch hydrolysate.

Indeed, as in the case of compositions which include fructose and starch hydrolysate, the preferred second film forming agent are solubilized keratin, an alginate and gum tragacanth. It is particularly preferred that the same concentration ranges apply. That is, preferred embodiments include those recited above with the proviso that a ribose sugar replaces fructose. Moreover, the same weight ratios of combined ribose to starch hydrolysate applies as in the case where combined fructose and starch hydrolysate are used above.

As in the case of the preferred composition which employs fructose, starch hydrolysate and a second film forming composition, other agents employed in the present invention may be included with the composition which comprises ribose, starch hydrolysate and second film forming agents, especially solubilized keratin, an alginate and gum tragacanth.

Those skilled in the art are aware that starch hydrolysate is a generic term of a mixture of carbohydrates most commonly classified according to its dextrose equivalent. The starch hydrolysate of the present invention is one which has a dextrose equivalent of no more than 85, but preferably no more than 40. More preferably, the dextrose equivalent of the starch hydrolysate of the present invention is between about 5 and 40. Still more preferably, the dextrose equivalent of the starch hydrolysate is between about 7.5 and 30. Yet still more preferred is a starch hydrolysate having a dextrose equivalent in the range of between about 10 and 20. Most preferably, the starch hydrolysate of the present invention has a dextrose equivalent in the range of between about 13 and 17. Those skilled in the art are aware that starch hydrolysates having a dextrose equivalent in this latter most preferred range are more specifically maltodextrins. It will also be understood that "pharmaceutically acceptable" means purified and sterilized. Any of the known methods, including dry heat, filtration, or irradiation may be used for the sterilization, although for the monosaccharide, irradiation is not particularly recommended because of the possible effect on the molecular structure.

The action of the film-forming agent combined with monosaccharide may be further enhanced by the incorporation of small amounts of optional ingredients. The optional components generally do not constitute more than 5% of the total weight of the composition In another preferred embodiment, a principal additional component of the composition of the present invention is one which includes ascorbic acid or a pharmaceutically acceptable salt thereof Those skilled in the art are aware that ascorbic acid or a pharmaceutically acceptable salt thereof promotes the formation and growth of healthy granulation tissue Among the pharmaceutically acceptable ascorbate salts contemplated for use in this invention are sodium ascorbate, potassium ascorbate and calcium ascorbate However, it is emphasized that the acid, ascorbic acid itself, is most preferred When employed, the ascorbate component is preferably used in an amount of from about 0.1-5% of the total weight of the composition, and most preferably comprises about 1-3.5% of the composition.

In another preferred embodiment, the composition of the present invention includes one or more pharmaceutically acceptable metal salts selected from the group consisting of iron, calcium, copper, magnesium, selenium, silver, manganese, zinc and mixtures thereof The incorporation of one or more of these salts in the composition of the present invention beneficiates the process of its healing Among the preferred salts, a ferrous (ion II) containing salt is most preferred. For example, the utilization of one of ferrous sulfate, ferrous chloride or ferrous gluconate is preferred. Of these, the use of ferrous sulfate is particularly preferred. It is emphasized that more than one of these salts may be included in the composition of the present invention. Thus, a ferrous salt may be used with one or more of the above recited class of metal salts. Of these, ferrous sulfate is particularly preferred. Among the other salts contemplated for use here are calcium ascorbate, calcium chloride, calcium iodate, calcium permanganate, calcium phosphate (mono-, di, and tribasic), calcium gluconate, zinc acetate, zinc carbonate, zinc chloride, zinc citrate, zinc iodate, zinc oxide, zinc permanganate, zinc proxide, zinc salicylate, zinc stearate, zinc sulfate, magnesium chloride, magnesium citrate, magnesium chloride, magnesium sulfate, manganese chloride and copper sulfate Preferred silver salts are silver nitrate, silver citrate, silver iodide and silver lactate. Iodine, in elemental form, and complexed with starch hydrolysate through heating and as iodine tincture, iodine salts, such as lugol solution, may also be added. Sodium and potassium iodide, sodium potassium iodate, calcium iodate and calcium iodide are particularly preferred. Dilute PVP-iodine solutions in water, normal saline on balanced salts solution may also be effectively employed in conjunction with the present treatment.

A further additional ingredient may be one or more of the adenosine phosphates, i.e., ATP, ADP or AMP.

In still yet another preferred embodiment of the composition of the present invention the composition includes a compound selected from the group consisting of alpha-ketoglutaric acid and pharmaceutically acceptable salts of alphaketoglutaric acid. Alpha-ketoglutaric acid and its salts accelerate collagen formation thus increasing the rate of healing of the wound to which the composition of the present invention is applied. This component is generally presnet in an amount of no more than 1-2%

Finally, yet another component may be included in the composition of the present invention. This component is one or more amino acids which also improve healing. In a preferred embodiment one or more, up to all, of the following amino acids may be provided in the composition of the present invention: isoleucine, leucine, lysine, methionine, phenylalanine, threonine, tryptophane, valine, tyrosine, alanine, arginine, glycine, proline, histidine, serine, asparagine, aspartic acid, cysteine, cystine, glutamine and glutamic acid. Of these, glycine, proline and lysine are particularly preferred.

It will be understood that, as used herein, the term "amino acid" refers to both the pure form and the hydrochloric acid salts of the amino acids. Thus, in preferred embodiments of the present invention wherein amino acid is employed, one, two or all three of the above preferred amino acids are included in the composition of this invention. In general, the amount of amino acid in the composition should not exceed 1%.

In a particularly preferred embodiment, the composition of the instant invention includes starch hydrolysate and a monosaccharide selected from the group consisting of d-fructose, d-glucose and d-sorbose. More preferably, the composition of the present invention comprises a starch hydrolysate having a dextrose equivalent of not more than 40, and d-fructose Preferably the fructose comprises up to about 30% of the total weight of the composition.

In other preferred embodiments, the composition comprising d-fructose and a starch hydrolysate having a dextrose equivalent of no more than 40 is supplemented with one or more of the following additives: an amino acid which is preferably one or more of the amino acids recited above; alpha-ketoglutaric acid or a pharmaceutically acceptable salt thereof; a ferrous salt, preferably ferrous sulfate; another pharmaceutically acceptable salt of a metal selected from the group consisting of calcium, zinc, manganese, magnesium, copper, selenium and silver In a particularly preferred embodiment of the present invention all of the above components are included in the composition. That is, a particularly preferred embodiment of the present invention is provided in a composition incorporating a principal amount of starch hydrolysate, having a dextrose equivalent between 13 and 17; d-fructose, present in a concentration of from 5 to 30 percent; ascorbic acid, present in the concentration of 1 to 5 percent; ferrous sulfate, present in a concentration of 0.1 to 1 percent; a zinc salt, present in a concentration of up to 1 percent; alphaketoglutarate present in a concentration of about 1-2% and at least one amino acid present in a concentration of 0.1 to 1 percent, all said percentages being by weight, based on the total weight of the composition.

In a wound which is only moderately infected or not yet infected, the inclusion of the monosaccharide is sufficient to control infection to acceptable levels. In the cases of particularly heavy infections, however, it may be desirable to also include, in small amounts one of the known antibiotics or antifungal agents commonly used in wound treatment. Among the useful antibiotics are streptomycin, penicillin, tetracycline, silver sulfadiazine, sulfanilamide, methylated sulfanilamide (sulfamylon®), cephalosporins, and amino-glycosides. Useful antifungal agents are nystatin, mycostatin®, or gramicidin. It must be noted that only small amounts of the antibiotic need be added.

The compositions of the present invention may be effectively employed in a regular program of wound treatment. For example, in the preferred method of wound treatment, a starch hydrolysate monosaccharide powder preparation is applied directly to the wound once or twice a day. Typically, the wound is first surgically debrided to remove all necrotic tissue. It is also possible to use water pulsating instruments to facilitate debridement; enzymatic debridement may prove useful as well, employing proteolytic enzymes such as Travase®, Biozyme®, collagenase or elase.

In accordance with the teachings of U.S Pat. No. 4,414,202, the wound is preferably irrigated, prior to application of the film forming composition, with a buffered salt solution having a pH between 6-7.8. It has also been found that irrigation and/or soaking the wound with dilute (0.05-0.1%) PVP-iodine solutions for 5 to 30 minutes before the addition of the composition aids in enhancing the effect of the dry material on wound healing. The wound is then covered with the starch hydrolysate/monosaccharide composition in an amount sufficient to allow formation of a film over the wound. The wound may then optionally be covered with a preferred non-adhesive dressing, which may be removed for the daily repeat of the treatment. This method of treatment is particularly applicable to mammalian skin wounds, and is most suitable for treatment of human wounds.

The following examples further illustrate the use of the present invention.

EXAMPLE 1

The following illustrative Examples of wound healing compositions of the present invention. In each case, fructose was a chemically pure fructose made by Pfanstiehl Laboratories, Inc. (Waukegan, Ill.) M-150 refers to a starch hydrolysate having a dextrose equivalent of 13-17 (Maltrin®, Grain Processing Corporation, Musczatine, Iowa). The starch hydrolysate was sterilized by radiation prior to use.

| I.  | M-150 | 95 g |
|     | fructose | 5 g |
| II. | M-150 | 70 g |
|     | fructose | 30 g |
| III.| M-150 | 88 g |
|     | fructose | 10 g |
|     | ascorbic acid | 2 g |
| IV. | M-150 | 72 g |
|     | fructose | 15 g |
|     | sodium ascorbate | 3 g |
| V.  | M-150 | 81 g |
|     | fructose | 15 g |
|     | ascorbic acid | 3 g |
|     | amino acids | 1 g |
|     | (20 amino acids in equal proportions) | |
| VI. | M-150 | 77 g |
|     | fructose | 20 g |
|     | potassium ascorbate | 2 g |
|     | glycine | .33 g |
|     | lysine | .33 g |
|     | proline | .34 g |
| VII.| M-150 | 80 g |
|     | fructose | 18 g |
|     | α-ketoglutarate | 1 g |
|     | ferrous sulfate | .1 g |
|     | amino acid | .9 g |
|     | (20 amino acids in equal proportions) | |

EXAMPLE 2

A. An 84-year-old white female was affected with progressive brain syndrome, Alzheimer's disease malnutrition, cachexia and a non-healing decubitus ulcer of the left ischiatic region. The ulcer measured, at time of admission, 5.5×6×1.8 cms. There were large amounts of foul-smelling, necrotic, gangrenous tissue Cultures taken from the wound indicated the presence of the following bacteria: *Proteus mirabilis, Escherichia coli, Staphylococcus aureus,* and *Pseudomonas aeruginosa*

Initially thorough debridement of necrotic tissue was carried out, followed by intensive irrigation with TIS-U-SOL®, a balanced salts solution The ulcerated area was then filled with M-150, a D-glucose polysaccharide (starch hydrolysate) with a dextrose equivalent of 13-17. Treatment thereafter consisted of twice daily irrigation with the salt solution, and application of the starch hydrolysate. The ulcer was covered each time with a non-adhesive dressing. After 3 weeks of treatment, the infection decreased and the ulcer decreased in size, but healing was progressing very slowly.

At this point, treatment was continued in the same fashion, but instead of the starch hydrolysate alone, a mixture of starch hydrolysate and fructose, in a ratio of 80:20, was used An immediate clinical response was manifested by more highly vascularized granulation tissue formation, a faster filling in of the crater, a rapid decrease in the surface area of the ulcer, and a faster growth of the epithelium. Further the exudate normally present in the ulcer decreased significantly, and the presence of a more sturdy, better organized, more clinging film over the granulation tissue was noticed Multiple strands of this film could be seen clinging to and binding several areas of the ulcer granulation tissue platform. By the end of 3 weeks (a total of six weeks) the ischiatic ulcer was completely healed.

B. A 67-year-old woman afflicted with multiple sclerosis of 12 years duration was completely paralyzed, and had developed severe, deep infected Stage IV pressure ulcers of both hips, the sacral area, and both ischiatic regions.

She was admitted to the wound healing unit and underwent the following treatment; twice daily irrigation with a balanced, buffered salt solution, and sprinkling of M-150 starch hydrolysate powder. Healing and infection control began on the first day of treatment; by the end of the third week, the ulcerated areas had healed about 20% of the initial size. At that point, the lesions on the right side were treated with a mixture of starch hydrolysate (73 parts), fructose (24 parts), ascorbic acid (2 parts) and a mixture of 20 amino acids in equal proportions (1 part). The left side lesions received the same treatment as before, and acted as controls. By the end of 8 weeks, the ulcers treated with the complex formulation were 90% healed, whereas the control areas were only 35% healed.

What is claimed is:

1. A composition comprising fructose, starch hydrolysate and a second film forming agent other than starch hydrolysate, said fructose and said starch hydrolysate present in a concentration such that the weight ratio of fructose to starch hydrolysate is in the range of between about 1:99 and about 15:85.

2. A composition in accordance with claim 1 wherein said second film forming agent is selected from the group consisting of polyvinyl pyrrolidone, solubilized keratin, alginate, gum tragacanth, gelatin, agar, pectin, cellulose, guar gum and locust bean gum.

3. A composition in accordance with claim 2 wherein said second film forming agent is selected from the group consisting of solubilized keratin, an alginate and gum tragacanth, said second film forming agent present in a concentration of between about 1% and about 99% and said fructose and said starch hydrolysate present in a combined concentration of between about 1% and about 99%, said percentages being by weight, based on the total weight of said fructose, starch hydrolysate and second film forming agent.

4. A composition in accordance with claim 3 wherein said combined fructose and starch hydrolysate are present in a concentration in the range of between about 50% and about 75% and said second film forming agent is present in a concentration in the range of between about 25% and about 50%.

5. A composition in accordance with claim 4 wherein said second film forming agent is solubilized keratin.

6. A composition in accordance with claim 4 wherein said second film forming agent is an alginate.

7. A composition in accordance with claim 4 wherein said second film forming agent is gum tragacanth.

8. A composition comprising ribose, starch hydrolysate and a second film forming agent other than starch hydrolysate, said fructose and said starch hydrolysate present in a concentration such that the weight ratio of fructose to starch hydrolysate is in the range of between about 1:99 and about 15:85.

9. A composition in accordance with claim 8 wherein said second film forming agent is selected from the group consisting of polyvinyl pyrrolidone, solubilized keratin, an alginate, gum tragacanth, gelatin, agar, pectin, cellulose, guar gum and locust bean gum.

10. A composition in accordance with claim 9 wherein said second film forming agent is selected from the group consisting of solubilized keratin, an alginate and gum tragacanth, said second film forming agent present in a concentration of between about 1% and about 99% and said fructose and starch hydrolysate present in a combined concentration of between about 1% and about 99%, said range of between about 50% and about 75% and percentage being by weight, based on the total weight of said ribose, starch hydrolysate and second film forming agent.

11. A composition in accordance with claim 10 wherein said ribose and said starch hydrolysate are present in a combined concentration in the range of between about 50% and about 75% and said second film forming agent is present in a concentration of between about 25% and about 50%.

12. A composition in accordance with claim 11 wherein said second film forming agent is solubilized keratin.

13. A composition in accordance with claim 11 wherein said second film forming agent is an alginate.

14. A composition in accordance with claim 11 wherein said second film forming agent is gum tragacanth.

* * * * *

UNITED STATES PATENT AND TRADEMARK OFFICE
CERTIFICATE OF CORRECTION

PATENT NO. : 5,177,065

DATED : January 5, 1993

INVENTOR(S) : A. N. Silvetti, Sr., et al.

It is certified that error appears in the above-identified patent and that said Letters Patent is hereby corrected as shown below:

```
        Column 1, line 9:   after "processes" insert --.--
        Column 1, line 20:  after "region" insert --.--
        Column 1, line 38:  "known." should read as
--known,--
        Column 5, line 30:  after "talose" insert --.--
        Column 6, line 39:  "to" should read as --and--
        Column 6, line 47:  "a bout" should read as
--about--
        Column 6, lines 57 & 60:  "to" should read as
--and--
        Column 6, line 61:  after "3:97" insert --and
about 25%--
        Column 7, line 60:  after "thereof" insert --.--
        Column 7, line 63:  after "tissue" insert --.--
        Column 7, line 66:  after "ascorbate" insert --.--
        Column 7, line 67:  after "preferred" insert --.--
        Column 8, line 8:   after "thereof" insert --.--
        Column 8, line 11:  after "healing" insert --.--
```

UNITED STATES PATENT AND TRADEMARK OFFICE
CERTIFICATE OF CORRECTION

PATENT NO. : 5,177,065

DATED : January 5, 1993

INVENTOR(S) : A. N. Silvetti, Sr., et al.

It is certified that error appears in the above-identified patent and that said Letters Patent is hereby corrected as shown below:

Column 8, line 28: after "sulfate" insert --.--

Column 8, line 51; after "1-2%" insert --.--

Column 9, line 9: after "d-fructose" insert --.--

Column 9, line 22: after "silver" insert --.--

Column 10, line 15: "illustrative" should read as --illustrate--

Column 10, line 60: after "aeruginosa" insert --.--

Column 10, line 63: after "solution" insert --.--

Column 11, line 7: after "used" insert --.--

Column 11, line 14: after "noticed" insert --.--

Column 12, line 34, Claim 10: before "starch" insert --said--

UNITED STATES PATENT AND TRADEMARK OFFICE
CERTIFICATE OF CORRECTION

PATENT NO. : 5,177,065

Page 3 of 3

DATED : January 5, 1993

INVENTOR(S) : A. N. Silvetti, Sr., et. al.

It is certified that error appears in the above-indentified patent and that said Letters Patent is hereby corrected as shown below:

Column 12, lines 36-37, Claim 10: delete "range of between about 50% and about 75% and percentage" and insert --percentages--

Signed and Sealed this

Twenty-fourth Day of January, 1995

Attest:

BRUCE LEHMAN

*Attesting Officer*  *Commissioner of Patents and Trademarks*